United States Patent [19]

Pai

[11] Patent Number: 5,072,477
[45] Date of Patent: Dec. 17, 1991

[54] STRUCTURE OF MOTORIZED TOOTHBRUSH WITH SERVING PERIOD INDICATION

[76] Inventor: Chung-Jen Pai, No. 2, Lane 255, Sec. 2 Chung Shan Rd., Pan Chiao City, Taipei, Taiwan

[21] Appl. No.: 532,049

[22] Filed: Jun. 1, 1990

[30] Foreign Application Priority Data

Jan. 24, 1990 [DE] Fed. Rep. of Germany ....... 9000747

[51] Int. Cl.⁵ .............................................. A46B 13/02
[52] U.S. Cl. .................................... 15/22.1; 15/167.1; 15/176.1; 15/176.6; 116/298; 116/308
[58] Field of Search ...................... 15/22.1, 23, 24, 28, 15/29, 167.1, 176.1, 176.6; 116/298, 308, 335; 40/314, 314 X, 335

[56] References Cited

U.S. PATENT DOCUMENTS

| 1,544,479 | 6/1925 | Penn | 40/335 |
| 1,553,258 | 9/1925 | Moore | 40/335 |
| 2,215,465 | 9/1940 | Ehrlich | 116/308 |
| 3,400,417 | 9/1968 | Moret | 15/22.1 |
| 4,466,150 | 8/1984 | Jurt | 15/167.1 |
| 4,592,109 | 6/1986 | Borea | 15/176.1 |

Primary Examiner—Harvey C. Hornsby
Assistant Examiner—Randall Chin
Attorney, Agent, or Firm—Bucknam and Archer

[57] ABSTRACT

A motorized toothbrush, which comprises a serving period indicating ring adjustably mounted on a brush handle and secured between a brush head and a power unit for the indication of the month a brand-new brush begins to use so that one can easily identify if a brush has been over-used.

1 Claim, 2 Drawing Sheets

FIG:1

STRUCTURE OF MOTORIZED TOOTHBRUSH WITH SERVING PERIOD INDICATION

BACKGROUND OF THE INVENTION

The present invention is related to motorized toothbrushes and more particularly to a motorized toothbrush which comprises a serving period indicating ring conveniently for identifying if a brush has been over-used.

According to medical report, the oral cavity hygiene has a great concern with one's health. Therefore, the teeth must be regularly cleaned so as to maintain in a good condition. The toothbrush is a device most suitable and commonly used for cleaning the teeth and irritating the gum. In recent years, motorized toothbrush has been popularly used by people because of its high cleaning effect through high vibration frequency. Either a regular or a motorized type of toothbrush is used, the bristles of a toothbrush may be damaged or contaminated with filth after a certain period in use. Therefore, a toothbrush of any type must be replaced with a new brush after having been used for a certain period of time. According to dentists' opinion, a normal toothbrush must be replaced after 3 months in use. The present invention is to help people identify if a toothbrush has been over-used.

SUMMARY OF THE INVENTION

The present invention has been accomplished under the circumstances in view. It is the main object of the present invention to provide a motorized toothbrush for cleaning the teeth, which can help people to identify if a toothbrush has been over-used.

According to the present invention, a motorized toothbrush comprises a power unit having a driving axle connected with a brush, and a serving period indicating ring adjustably set between the brush and the power unit. An index is marked on the lower end of the brush pointed at a specific marking made on the periphery of the serving period indicating ring. By means of the indication of a specific marking which designates a month of a year, one can easily identify how long the toothbrush has been approximately used.

BRIEF DESCRIPTION OF THE DRAWINGS

The present invention will now be described by way of example with reference to the annexed drawings, in which.

DETAILED DESCRIPTION OF THE PREFERRED EMBODIMENT

Figure 1:
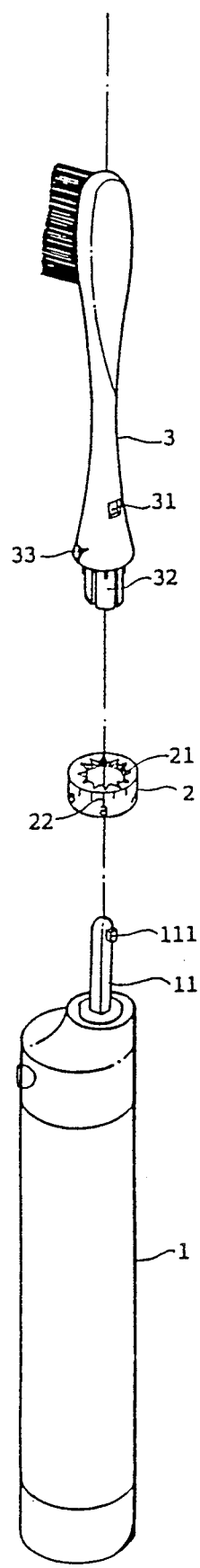
FIG. 1 is a perspective fragmentary view of the present invention.

Referring to the annexed drawings in greater detail, therein, illustrated is a motorized toothbrush embodying the present invention and generally comprised of a power unit 1, a serving period indicating ring 2, and a brush head 3.

The power unit 1 comprises a housing having received therein a motor connected in series with a battery to drive a driving axle 11 to rotate. The driving axle 11 extends vertically upward from the housing of the power unit 1 and comprises a tenon 111 horizontally extending therefrom at an upper position.

The serving period indicating ring 2 is a ring plate having teeth 21 on its inner wall and markings 22 around its periphery, in which the markings 22 are respectively for the indication of the months of a year, for example, the markings 22 can be numerals of 3, 6, 9 and 12 to respectively represent March, June, September and December.

The brush head 3 has a plurality of bundles of bristles vertically fastened therein at one end, a plurality of projecting strips 32 axially extending downward therefrom at the opposite end around a circle, a hole 31 on its outer wall at a suitable location, and an index 33 on its outer wall near the projecting strips 32. The projecting strips 32 are designed and disposed in such a manner that the driving axle 11 is permitted to be inserted in the brush head 3 with its tenon 111 fastened in the hole 31 of the brush head 3 after projecting strips 32 are inserted in the serving period indicating ring 2. Therefore, the brush head 3 can be firmly secured to the power unit 1 by means of the engagement of the tenon 111 with the hole 31, with the serving period indicating ring 2 set therebetween and below the index 33 for period indication.

Figure 2:
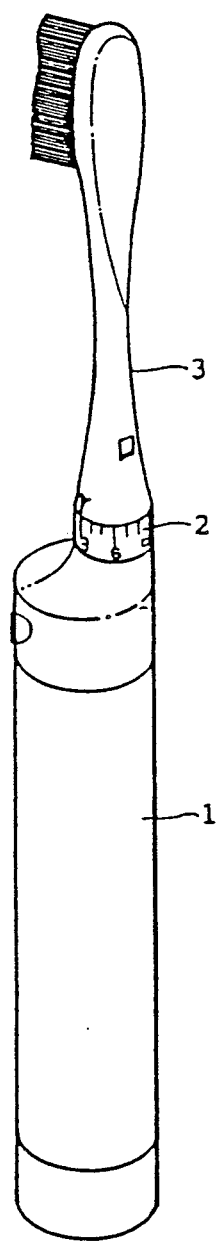
FIG. 2 is a perspective assembly view thereof.

Referring to FIG. 2 again, when a brand-new brush head 3 of the present invention is to be used in March, the projecting strips 32 of a brush head 3 are inserted through the serving period indicating ring 2 with the index 33 pointed at one of the markings 22 of the serving period indicating ring 2 which is designated for March, and then the driving axle 11 of the power unit 1 is inserted in the projecting strips 32 of the brush head 3 permitting the tenon 111 of the driving axle 11 to fasten in the hole 31 of such a brush head 3. As soon as June comes, the used brush head 3 is thrown away and a new piece of brush head 3 is replaced to match with the serving period indicating ring 2.

By means of the above-described arrangement, one can easily make sure if a toothbrush has been used over a fixed period.

The above description is for better understanding of the present invention and not intended as a definition of the limits and scope of the invention disclosed. Recognizing that various modifications been apparent the scope herein shall be deemed as defined in the claim set forth hereinafter.

I claim:

1. A motorized toothbrush, comprising: a brush head comprising a plurality of bundles of bristles vertically fastened therein at one end, a plurality of projecting strips axially extending downwardly therefrom at the opposite end around a circle, a hole on the outer suface of said brush head, and an index near said projecting strips; a power unit comprising a housing, motor in the interior thereof, said motor being connected in series with a battery, a driving axle vertically extending upwardly from said housing and comprising a tenon horizontally extending therefrom at an upper position thereof, said motor driving said axle and causing said axle to rotate, a serving period indicating ring comprising teeth on its inner wall and markings around its periphery corresponding to said teeth and respectively for the indication of each of the months of a year; said driving axle being inserted in the projecting strips whereby said tenon enters into said hole in said brush head, said projecting strips enter said ring and are held by said teeth, and said index is pointed at one of said markings.

* * * * *